United States Patent
Mousavi et al.

(10) Patent No.: US 12,019,074 B2
(45) Date of Patent: Jun. 25, 2024

(54) METHOD OF ANALYSING A SAMPLE FOR AT LEAST ONE ANALYTE

(71) Applicant: LUMITO AB, Lund (SE)

(72) Inventors: Monirehalsalat Mousavi, Lund (SE); Urban Widén, Helsingborg (SE); Anders Sjögren, Lund (SE)

(73) Assignee: LUMITO AB, Lund (SE)

( * ) Notice: Subject to any disclaimer, the term of this patent is extended or adjusted under 35 U.S.C. 154(b) by 0 days.

(21) Appl. No.: 16/620,482

(22) PCT Filed: Jun. 8, 2018

(86) PCT No.: PCT/EP2018/065247
§ 371 (c)(1),
(2) Date: Dec. 12, 2019

(87) PCT Pub. No.: WO2018/224688
PCT Pub. Date: Dec. 13, 2018

(65) Prior Publication Data
US 2020/0182881 A1 Jun. 11, 2020

(51) Int. Cl.
*G01N 33/58* (2006.01)
*C12Q 1/6886* (2018.01)
(Continued)

(52) U.S. Cl.
CPC ......... *G01N 33/585* (2013.01); *C12Q 1/6886* (2013.01); *G01N 1/30* (2013.01); *G01N 33/5005* (2013.01); *G01N 33/543* (2013.01)

(58) Field of Classification Search
None
See application file for complete search history.

(56) References Cited

U.S. PATENT DOCUMENTS

| 5,736,410 A | 4/1998 | Zarling et al. |
| 2004/0239916 A1* | 12/2004 | Seino ................. G01N 21/6456 356/28.5 |

(Continued)

FOREIGN PATENT DOCUMENTS

WO 2016127149 A2 8/2016

OTHER PUBLICATIONS

Jiang S, Zhang Y, Lim KM, Sim EKW and Ye L. Nanotechnology 20 (2009) 155101 (9pp) NIR-to-visible upconversion nanoparticles for fluorescent labeling and targeted delivery of siRNA. Nanotechnology;2009;20: 155101 (9pp) (Year: 2009).*

(Continued)

*Primary Examiner* — Ann Montgomery
*Assistant Examiner* — Chau N. B. Tran
(74) *Attorney, Agent, or Firm* — Veros Legal Solutions, LLP

(57) ABSTRACT

A method of analysing a sample for at least one analyte in histology, such as histopathology, or cytopathology, particularly for immunohistochemistry or immunocyto-chemistry is described. The method comprising contacting the sample with at least one targeting moiety or probe, wherein each different targeting moiety or probe of the at least one targeting moiety or probe specifically binds a different analyte of the at least one analyte. Each different targeting moiety or probe of said at least one targeting moiety or probe is conjugated to a different luminescent particle. Detecting a signal from the luminescent particle associated with the at least one targeting moiety bound to the sample. The presence or amount of at least one analyte may thereby be detected in the sample.

20 Claims, 5 Drawing Sheets

(51) Int. Cl.
*G01N 1/30* (2006.01)
*G01N 33/50* (2006.01)
*G01N 33/543* (2006.01)

(56) References Cited

U.S. PATENT DOCUMENTS

| | | | | |
|---|---|---|---|---|
| 2006/0194220 | A1* | 8/2006 | Reddy | A61P 35/00 |
| | | | | 435/6.14 |
| 2008/0118944 | A1* | 5/2008 | Larsen | G01N 33/53 |
| | | | | 435/6.17 |
| 2010/0045698 | A1* | 2/2010 | Shields | G16H 40/67 |
| | | | | 345/629 |
| 2012/0252685 | A1* | 10/2012 | Treynor | G01N 33/6803 |
| | | | | 435/6.19 |
| 2013/0044933 | A1* | 2/2013 | Kenny | G01N 21/6458 |
| | | | | 382/133 |
| 2013/0171623 | A1* | 7/2013 | He | G01N 33/582 |
| | | | | 435/5 |
| 2013/0178392 | A1* | 7/2013 | Sood | G01N 1/30 |
| | | | | 506/9 |
| 2014/0120534 | A1* | 5/2014 | Bernitz | C12Q 1/6841 |
| | | | | 435/6.11 |
| 2015/0004598 | A1 | 1/2015 | Gao et al. | |
| 2015/0353821 | A1* | 12/2015 | Zhang | A61K 47/02 |
| | | | | 424/489 |
| 2017/0176318 | A1* | 6/2017 | Scarcelli | G01N 15/147 |
| 2017/0299482 | A1* | 10/2017 | Gupta | G01N 1/30 |

OTHER PUBLICATIONS

Anonymous: "Microscopy with UV surface excitation—Wikipedia", May 7, 2019 (May 7, 2019), XP055586352, Retrieved from the Internet: URL: https://en.wikipedia.org/wiki/Microscopy_with_UV_surface_excitation.
Dalong Ni, et al., Dual-Targeting Upconversion Nanoprobes across the Blood-Brain Barrier for Magnetic Resonance/Fluorescence Imaging of Intracranial Glioblastoma, ACS Nano 2014, 8, 2, 1231-1242, Jan. 7, 2014, https://doi.org/10.1021/nn406197c, ISSN: 1936-0851, DOI: 10.1021/nn406197c, figures 1,2,5.
Hanjie Wang, et al. MC540 and Upconverting Nanocrystal Coloaded Polymeric Liposome for Near-Infrared Light-Triggered Photodynamic Therapy and Cell Fluorescent Imaging, ACS Applied Materials & Interfaces 2014 6 (5), 3219-3225, DOI: 10.1021/am500097f.
Hou, Zhiyao et al. 808 nm Light-triggered and hyaluronic acid-targeted dual-photosensitizers nanoplatform by fully utilizing Nd(3+)-sensitized upconversion emission with enhanced anti-tumor efficacy, Biomaterials 101 (2016): 32-46, ISSN: 0142-9612, DOI: 10.1016/j.biomaterials.2016.05.024 p. 33 right column; abstract; figures 2b, c.
International Preliminary Report on Patentability mailed Aug. 5, 2019 in PCT/EP2018/065247.
International Search Report mailed Jul. 30, 2018 in PCT/EP2018/065247.
Lang Rao, et al. Effective cancer targeting and imaging using macrophage membrane-camouflaged upconversion nanoparticles, J Biomed Mater Res A. Feb. 2017;105(2):521-530. doi: 10.1002/jbm.a.35927. Epub Nov. 3, 2016., DOI: 10.1002/jbm.a.35927.
Lang Rao, et al: Erythrocyte Membrane-Coated Upconversion Nanoparticles with Minimal Protein Adsorption for Enhanced Tumor Imaging, ACS Applied Materials & Interfaces 2017 9 (3), 2159-2168, DOI: 10.1021/acsami.6b14450.
Lucky, Sasidharan Swarnalatha et al. "In vivo Biocompatibility, Biodistribution and Therapeutic Efficiency of Titania Coated Upconversion Nanoparticles for Photodynamic Therapy of Solid Oral Cancers." Theranostics vol. 6,11 1844-65. Jul. 18, 2016, doi:10.7150/thno.15088.
Written Opinion of the International Searching Authority mailed Jul. 30, 2018 in PCT/EP2018/065247.
Zhou, L., Wang, R., Yao, C. et al. Single-band upconversion nanoprobes for multiplexed simultaneous in situ molecular mapping of cancer biomarkers. Nat Commun 6, 6938 (2015) doi:10.1038/ncomms7938.
European Search Report mailed Mar. 16, 2021 in EP Patent Application No. 20196330.3, filed Jun. 8, 2018.
Li, Xiyu, et al: Yb3+/Ho3+ Co-Doped Apatite Upconversion Nanoparticles to Distinguish Implanted Material from Bone Tissue. ACS Applied Materials & Interfaces 2016 8, 27458-27464, DOI: 10.1021/acsami.6b05514.
Opinion of the European Searching Authority dated Jul. 26, 2022 in Application 20196330.3.

\* cited by examiner

METHOD OF ANALYSING A SAMPLE FOR AT LEAST ONE ANALYTE

BACKGROUND OF THE INVENTION

Field of the Invention

This disclosure pertains in general to analyse a sample for at least one analyte. More particularly, the disclosure relates to colouring or staining a sample, such as tissue, with luminescent particles to determine the present or amount of at least one analyte in the sample. Especially, the disclosure relates to colouring or staining a sample with luminescent particles for histology, such as histopathology, or cytopathology, particularly for immunohistochemistry or immunocytochemistry.

Background of the Disclosure

In histology, such as histopathology, or cytology, such as cytopathology, several techniques are used to study and analyse biological cells or tissues, for instance immunohistochemistry (IHC) or immunocytochemistry (ICC).

In immunohistochemistry, antigens, such as proteins, are detected in cells on a sample of cells or a slice of tissue. The antigens are detected by using labelled antibodies that bind to specific antigens in the biological cells or tissue. In histology, such as histopathology, or cytology, such as cytopathology, colouring or staining, for example Haematoxylin-eosin (H&E), immunohistochemistry/immunocytochemistry (IHC/ICC) or hybridizations, such as In Situ Hybridization (ISH), are conventional standard routines for diagnosing atypical biological cells, such as in areas with tumours or apoptosis. Colouring or staining, such as immunohistochemistry or immunocytochemistry, is also commonly used in basic research to understand distribution and localization of biomarkers and differentially expressed genes and proteins in different parts of biological tissue. The bond between antibodies and antigens may be visualised in different ways. The most common practice is to conjugate, for example and antibody, to an enzyme, such as peroxidase, which may catalyse a colour change in a sample. An alternative is to label the antibodies with a fluorophore, such as fluorescein or rhodamine. The uses of fluorophores are restricted due to auto-fluorescence, i.e. fluorescence from the tissue itself, and require special and time-consuming preparations of the tissue sample to be useful. When using fluorophores, the conventional and preferred procedure based on formalin fixation and paraffin embedding suffers from even higher levels of auto-fluorescence than from the unprocessed tissue.

Other known drawbacks with traditional colouring and staining method are too strong background staining or weak target staining. Other drawbacks are that some stains or dyes, for example used for counterstaining for IHC/ICC, may have a fluorescence that interfere with reporters used for locating specific analytes. There are also some stains or dyes, for example used for counterstaining for IHC/ICC, that may absorb in a wavelength range that interfere either with the excitation or the emission of some reporters used for locating specific analytes.

These issues may decrease the contrast and resolution of the images used for diagnosis of a sample. One example is the commonly used haematoxylin and eosin both chromophores have strong absorbance in the visible region and eosin is highly fluorescent over much of the visible spectrum. This means that a single section cannot be co-stained with most types of immunofluorescence for IHC/ICC or hybridizations. Co-staining haematoxylin and/or eosin (H&E) with coloured pigment for colorimetric IHC/ICC or hybridization may also be a problem since these may be opaque and obscure the counterstaining, such as H&E staining. There are also the issues of spectral overlap both when doing chromogenic imaging or a fluorescence imaging, which means that the spectra of the labelling reporters and the counterstaining dye is so close that they cannot be resolved or distinguished between.

To overcome these problems counterstained images and IHC/ICC/hybridization images are routinely correlated to one another through serial sectioning and imaging of complimentary regions on different sections of the same tissue specimen, but these methods suffer alignment impediments due to the fact that staining is completed on sections that are at best 3-10 µm apart. The same applies when multiplexing for detecting more than one analyte where each analyte often requires its own section. Multiple consecutive sections may not only cause problem with co-registration but requires a larger sample, such as a thicker tissue section or biopsy, or more cells, than normally obtained.

On top of these issues, there are other things that need to be considered such as photo-bleaching and that different dyes, stains and reporters may react with each other and become chemically unstable and lose their properties.

A vast array of chromogenic and fluorescent dyes has been developed to fit different experimental designs. These dyes can either be non-specific, staining most of the cells in the same way, or specific, selectively staining particular cellular compartments or chemical molecules within cells/tissues. Also, different protocols have been developed to help to overcome some of these drawbacks. Many of these protocols are complicated and time-consuming and include compromises.

An alternative to conventional labelling reporters for IHC/ICC and hybridization, quantum dots have been used and tried. Even though a lot of publications have been showing good results and quantum dots have been readily and commercially available on the market for a long time (almost 20 years), they are still not used in normal routines but mainly used for research. There has been reports that reasons may be issues related to, for example, stability compared to traditional small molecule dyes and stains, especially for the larger quantum dot particles with longer wavelengths, "Evaluation of quantum dot conjugated antibodies for immunofluorescent labelling of cellular targets" Jennifer E. Francis et al, Nanotechnol. 2017, 8, 1238-1249. Most of the successful studies have been done in the UV/deep blue and visible region (about 400 nm to 700 nm) where the main advantage of the quantum dots over more standard types of dyes and stains are the narrower fluorescence bands which normally is in the range of around 10 to 20 nm.

It is a desire to have an improved and simplified procedure that can save time and cost when analysing samples for analytes. A further desire would be to have the option of doing multiple colouring or staining for simultaneous analysis of a sample for more than one analyte. A further desire is to be able to perform examination of a small amount of sample.

SUMMARY OF THE INVENTION

Accordingly, examples of the present disclosure preferably seek to mitigate, alleviate or eliminate one or more deficiencies, disadvantages or issues in the art, such as the above-identified, singly or in any combination by providing a device, system or method according to the appended patent claims for analysing a sample for at least one analyte.

The disclosure relates to colouring or staining a sample using target specific moieties or probes. The target specific moieties or probes may be conjugated to luminescent particles, such as fluorescent particles, such as upconverting particles (such as upconverting nanoparticles), or other particles, such as quantum dots.

Each type of moiety or probe used may be conjugated to a different kind of luminescent particles. Hence multiple colouring or staining may be applied, thereby more than one type of analyte may be analysed in the same sample, such as from the same section. For example, the targeting moieties or probes may be used for determining the distribution or the concentration of different analytes in a sample. Further, the distribution of the analytes in the sample may also be determined in two or three dimensions.

The analysed sample may be a sample of biological cells or tissue. In some examples, the analysis is histopathology, in particularly immunohistochemistry, or cytopathology, in particularly immunocytochemistry, or hybridization for detecting at least one analyte, such as antigens or proteins, in cells of a sample, such as in a section of tissue. The sample may be prepared using a conventional procedure of formalin fixation and paraffin embedding.

The sample, such as a section of tissue, may then be viewed using a microscope or another type of imaging instrument, such as a high-resolution camera.

Alternatively, in some examples, the sample for histopathology, particularly immunohistochemistry, or cytopathology, particularly immunocytochemistry, or hybridization may be prepared using conventional freezing and slicing procedures, it may also be a free-floating section or similar known to the person skilled in the art.

In some examples of the disclosure, the samples may be liquid samples, such as body fluids, such as blood or plasma. Additionally, in some examples, the analysis may be used for biochemistry, such as using ELISA, such as micro-ELISA. Additionally, in some examples, the analysis may be used for microbiology.

The samples may be analysed for target analytes being, for example, antigens, antibodies, proteins, cellulose (cell membrane), carbohydrates (such as saccharides), or nucleic acid (e.g. DNA or RNA).

The samples may be analysed using fluorescence-microscopy. The fluorescence-microscopy may be digitalised and/or automatic.

In some examples, the analysis of the sample may be used for providing support in diagnosing a subject, such as a human or animal.

In one aspect of the disclosure, a method of imaging least one analyte in a biological sample is disclosed. The method comprising contacting the sample with at least one targeting moiety or probe, wherein each different targeting moiety or probes of the at least one targeting moiety or probe specifically may bind a different analyte of the at least one analyte, and wherein each different targeting moiety or probe of the at least one targeting moiety or probe may be labelled with a different luminescent particle. The luminescent particle may be an upconverting particle.

The method may further include obtaining a first image by detecting a signal from the luminescent particle associated with the at least one targeting moiety or probe bound to said sample.

Also, the method may include obtaining a second image from the sample, wherein the second image is a bright-field image of the sample without counterstain. The second image may in some examples be an image of the sample counterstained or coloured using a dye or stain.

Further, the method may include combining the first image with the second image to obtain a combined image.

In some example of the disclosure, the sample may be counterstained or coloured using a conventional dye or stain.

In some examples of the disclosure may the method relates to histology, such as immunohistochemistry (IHC), or cytology, such as immunocytochemistry (ICC), or hybridizations, such as In Situ Hybridization (ISH).

In some examples of the disclosure may the probe be a complementary DNA, RNA or modified nucleic acids strand that localize the at least one analyte being a DNA or RNA sequence.

In some examples of the disclosure may the method include analysing the combined image for detecting a presence or amount of the at least one analyte.

In some examples of the disclosure may the second image of the counterstained sample be obtained using, MUSE, bright-field or fluorescence depending on type of counterstain used.

The main advantages with the disclosed method are that no background may be picked up during the detection since the fluorescent light from the particles may fluoresce at a different wavelength than the auto-fluorescent light from the background. The auto-fluorescent light may origin from the sample itself, such as from the tissue, or from materials introduced in the process of preparing the sample, such as from the fixation and paraffin embedding. The emission of the luminescent particles, such as the fluorescent particles may be anti-Stokes shifted or Stokes shifted, for examples are upconverting particles (such as upconverting nanoparticles) normally anti-Stokes shifted and quantum dots Stokes-shifted. The Stokes or anti-Stokes shift may be used to spectrally filter out signal from the particles from the background. The background may consist of light from a light source, for instance the light source illuminating the sample, or light sources in the laboratory environment, or from fluorescence from the sample itself (auto-fluorescence) or other fluorescent molecules, substances or particles that are intentionally or non-intentionally existing in the sample. A conventional procedure may thereby be used, which will save time and cost compared to the procedures involving standard fluorophores.

A further advantage is that multiple colouring or staining is possible simultaneously, as the emission spectrum from each kind of luminescent particles, such as the fluorescent particles used may be very narrow. For example, by using differently doped upconverting particles (such as upconverting nanoparticles), or different types of quantum dots distinguishable emission spectra may be obtained. Each emission spectra will relate to a specific type of particle which bound to a specific target.

The use of luminescent particles, such as fluorescent particles, that are anti-Stokes shifted or Stokes shifted may increase the contrast. Also, the use of luminescent particles, such as fluorescent particles, that are anti-Stokes shifted or Stokes shifted may increase the resolution. This may be used for improving digitalised analyses and allow for automatization of the analyses.

Another advantage is that photobleaching may be prevented.

The method may be used for human samples or samples from animals.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings.

DESCRIPTION OF EXAMPLES

The following disclosure focuses on examples of the present disclosure applicable to determining the concentration or distribution of analytes in samples. The sample may be placed on transparent slides that are suitable for fluorescent microscopy. The disclosure may be especially advantageous for histology, such as histopathology, and in particularly immunohistochemistry (IHC). The disclosure may further be advantageous for cytology, such as cytopathology, and immunocytochemistry (ICC). The disclosure may also be advantageous for hybridization, such as in situ hybridization, and in particular fluorescent in situ hybridization (FISH). However, it will be appreciated that the description is not limited to this application but may be applied to many other types of analysis, samples, moieties, and targets.

Figure 1:
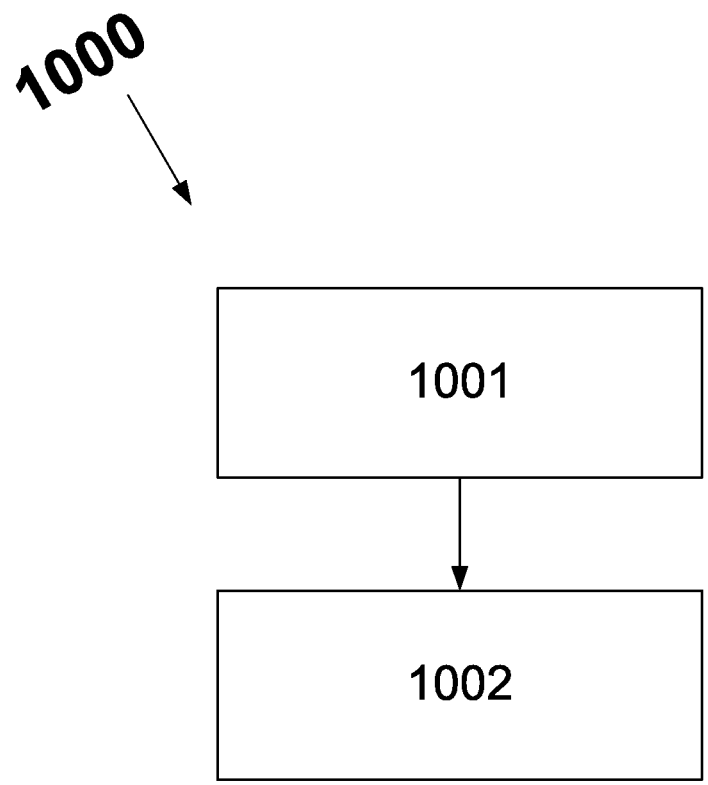
FIG. 1 is illustrating an example of a method of analysing a sample for at least one analyte.

FIG. 1 is illustrating a method 1000 of analysing a sample for at least one analyte. The sample may be biological sample, such as a slice of tissue, a sample of cells, or liquid samples to be viewed under microscope, such as fluorescence microscopy. The method comprising contacting 1001 the sample with at least one targeting moiety or a probe. Each different targeting moiety or probe of the at least one targeting moiety or probe specifically binds a different analyte of the at least one analyte in the sample. Further, the targeting moiety or probe of the at least one targeting moiety or probe is labelled with one or several luminescent particles, such as conjugated to luminescent particles, such as fluorescent particles, such as upconverting particles, such as upconverting nanoparticles, or quantum dots.

The luminescent particles are a class of contrast agents for bio-imaging. The luminescent particles, such as fluorescent particles may emit Stokes or anti-Stokes shifted light when excited at particular wavelengths. For example, particles may emit anti-Stokes shifted light (such as visible light) when excited at a particular wavelength, such as infrared or near-infrared light, for example at 975 nm. Additionally and/or alternatively, some upconverting particles may also emit Stokes shifted fluorescent light at a longer wavelength in the infrared or near-infrared light, such as around 1500 nm. This light may also be used as it is outside of the wavelength range of auto-fluorescent light emitted from the background, such as from the biological sample itself, such as tissue, or from the fixation and embedding of the sample. In some examples, emitted Stokes and anti-Stokes shifted light from the same particles may be used when analysing the sample.

Examples of Stokes shifted quantum dots may be excited by light in the UV-region (such as below 350 nm). They may also be excited by light in the red or near-IR region (such as 800 nm) where the tissue penetration depth is relatively large. The particles will emit light at a much longer wavelength than the excitation light preferably in a wavelength region where the auto-fluorescence is much weaker. For particles excited in the UV-region the emitted light may be in the visible region and for particles excited in the red or near infra read region the emitted light may be in the near infrared or infrared region, such as at around 1500 nm or longer.

The Stokes or anti-Stokes shift may provide an improved contrast signal compared to conventional fluorophores, as the auto-fluorescence from the tissue may be eliminated using filters. Especially tissue that is paraffin embedded has a strong background auto-fluorescence that makes it hard to use conventional fluorophores as labels without time consuming and costly preparations of the samples. Hence, apart from improving the contrast, luminescent particles, such as fluorescent particles, such as upconverting particles (such as upconverting nanoparticles), or quantum dots, may save time and cost as conventional formalin fixation and paraffin embedding may be used. The labelled target moiety or probes may be used in histology, such as histopathology and in particular immunohistochemistry, or cytology, such as cytopathology and in particular immunocytochemistry, or hybridizations, such as in situ hybridization (ISH), in combination with counterstaining, such as standard counterstaining used in histology, and in particularly immunohistochemistry, cytology, and in particularly immunocytochemistry, or hybridizations, such as in situ hybridization (ISH). Different detection method may be used such as bright-field fluorescence or MUSE. MUSE uses Ultraviolet light, for example at about 280 nm, from an LED arranged to provide oblique illumination. The light is used to excite just the surface layer of tissue that has been briefly (~10 seconds) stained using fluorescent dyes. Unlike light of longer wavelength, 280-nm light only penetrates to a depth of 10 microns or less, and thus excites fluorescent signals, conveniently in the visible range, only from the cut specimen surface. The images, which can be diffraction-limited, are captured using conventional microscope optics and a standard colour camera. Standard counterstains may be chromogenic or based on fluorescence. The dyes or stains may either be non-specific, staining most of the cells in the same way, or specific, selectively staining particular organells or cellular compartments or chemical molecules within cells/tissues, such as the nuclear by targeting nuclear acids cell walls or membranes. Examples of counterstains are, Haematoxylin and Eosin (H&E) staining, either each alone or combined, DAPI, Hoechst stain, Methyl green, Methylene blue, toluidine blue, DRAQ5, DRAQ7, Neuclear fast Red, Gram staining, PAS staining, Rhodamine, Nile blue, Nile red, Propidium iodide, SYTOX green, and many more known by the person skilled in the art.

Most upconverting particles are non-linear fluorophores. In the context of the present application, a "non-linear marker" is a luminescent marker, wherein a luminescence (L) of the marker is not linearly dependent on the radiant flux of excitation light (E). Non-linear markers thus have a luminescence according to: $L=k*E\hat{}x$, wherein $x>1$, and wherein k is a positive constant. The non-linear markers may also have a luminescence according to the following relationships:

$L=k*E\hat{}x+b$, $L=k(E)*E\hat{}x+b$, $L=k(E)*E\hat{}x+b(E)$, or $L=k*E\hat{}x+b(E)$, where k and b are material constants that are either constant or depending on the local field of excitation light (E), i.e. for k(E) and b(E). In comparison to conventional luminescence imaging, non-linear markers (or fluorophores) may thus require more than one photon for excitation. This may drastically decrease the excitation volume and provides a more localized excitation point. In this manner, contrast and resolution of luminescent imaging is improved. This may also improve, contrast and resolution of the emitted fluorescent light signal in luminescent imaging of absorbing and scattering media. Examples of the present invention may take advantage of this effect.

The excitation light is preferably pulsed and each pulse may be from a few μs to a couple of ms, such as 10 μs to 10 ms, such as such as 100 μs to 10 ms, such as 100 μs to 1 ms, such as 10 μs to 1 ms, such as 100 μs to 100 ms, such as 1 ms to 10 ms, such as 1 ms to 100 ms, which have shown to archive a higher yield in the signal relative to the excitation power compared to shorter excitation signals, such as ns, ps, fs.

Upconverting particles (such as nanosized upconverting particles) are for instance lanthanide doped oxides, for example diyttrium trioxide ($Y_2O_3$), which are easy to fabricate. Other upconverting particles (such as nanosized upconverting particles) are for instance lanthanide doped fluorides, which may have higher efficiencies than oxides. The higher efficiencies may be explained by the low phonon energies in fluorides, which lower the probability for non-radiative decay.

Further upconverting particles (such as upconverting nanoparticles) are for instance made of sodium yttrium tetrafluoride ($NaYF_4$), co-doped with either $Yb^{3+}/Er^{3+}$ or $Yb^{3+}/Tm^{3+}$. $NaYF_4$ can crystallize in two phases, cubic or hexagonal, called $\alpha$-$NaYF_4$ and $\beta$-$NaYF_4$, respectively. The upconverted luminescence from the $\beta$-phase material is approximately one order of magnitude higher compared to the upconverted luminescence from the $\alpha$-phase.

The non-linear fluorophores may be water soluble, allowing for easy administration in certain applications, such as in solutions for intravenous, peroral, or enteral administration.

A way to provide upconverting particles as water soluble, is to coat the particles with a structure that is polar, such as hydrophilic. Coatings may for instance be made of polymers or silica. Both synthetic polymers, for example, Polyethylene glycol (PEG), and natural polymers may be used for the coating. These polymers are stable in biological environments and do not interfere with the optical properties of the crystals, such as nanocrystals, in any significant negative way.

Water soluble upconverting particles may be provided without coatings. Hydroxyl groups may be attached to the surfaces of the upconverting particles, either by chemical bonds or physical absorption. Hydroxyl groups are by definition formed by covalent binding, and the final structure has polar properties.

Advantages of using upconverting particles are that biological samples, such as sections of tissue, should preferably be able to be stored for a long time and upconverting particles has a long lifetime. Upconverting particles will not easily photo-bleach and are very stable and will not react with other dyes and stains. This means that a sample can be stored for one month or longer and the analysis may still be repeated.

In some examples, the at least one targeting moiety may be an analyte specific ligand, such as a tumour-specific ligand. The ligand binds a receptor at the target analyte and different ligands may bind to different receptors at different target analytes. In some examples, the at least one targeting moiety such as a ligand, may be an antibody, an antigen, a hormone, a drug, a fragment antigen binding, an affibody molecule, an enzyme, a protein, or a peptide. Fragment antigen-binding is a region of an antibody that binds to an antigen generated in laboratory, examples are Fc, F(ab'), F(ab')$_2$ or Fab.

Affibody molecules are small proteins engineered to bind to target peptides or proteins with high affinity, imitating monoclonal antibodies. Affibody molecules are therefore considered antibody mimetics which are normally organic compounds that, like antibodies, may specifically bind antigens but are not structurally related to antibodies. They are usually artificial peptides or proteins. Nucleic acids or small molecules are sometimes considered antibody mimetics too. Common advantages over antibodies are better solubility, tissue penetration and low production costs.

Probes may be complementary DNA, RNA or modified nucleic acids strand used for to localizing a specific DNA or RNA sequence in a portion or section of a sample. Probes are normally used for in-situ hybridization.

By having each different type of targeting moiety or probes used for colouring or staining the sample labelled, for example conjugated, to different upconverting particles (such as upconverting nanoparticles) multiple analytes may be detected simultaneously in a sample. For example, the emission from upconverting particles (such as upconverting nanoparticles) are very narrow in the range 10 to 20 nm, and different kinds of particles may have very distinguishable emission spectra. Hence the particles may provide the possibility to detect and analyse multiple analytes in a sample simultaneously as there is no overlap in the colouring or staining of the different analytes. This is normally not possible with conventional colouring or staining techniques where fluorophores or colour staining are used. Especially not when using paraffin embedding techniques. Alternatives to using paraffin is frozen or free-floating sections.

The targeting moiety or probe may be conjugated to the upconverting particles using different methods, for example the targeting moieties or probe may be directly conjugated to the upconverting particle by covalent or non-covalent chemistry. Alternatively, and/or additionally, in some examples, the targeting moiety or probe may be conjugated to the upconverting particles by linker chemistry, such as using an adaptor molecule to link the targeting moieties or probe to upconverting particles.

Further, functionalization of the upconverting particles may be made in similar ways than functionalizing quantum dots, such as described in X. Gao et. al., In vivo cancer targeting and imaging with semiconductor quantum dots, Nature Biotechnology, 22, 8:969-976, 2004, which is incorporated herein in its entirety for all purposes. In Gao et. al. methods are described that are applicable on upconverting rare-earth doped particles (such as nanoparticles). The upconverting particles used in an example in this disclosure were $NaYF_4$-crystals prepared according to the method described in G. Yi et. al., Synthesis, characterization, and biological application of size-controlled crystalline (such as nanocrystalline) $NaYF_4$:Yb,Er infrared-to-visible upconversion phosphors. Nano Letters, 4, 11:2191-2196, 2004, doped with a combination of $Yb^{3+}$ and $Tm^{3+}$.

After the sample has been coloured or stained, a signal may be detected 1002 from the upconverting particles associated with the at least one targeting moiety or probe bound to the sample. The presence, distribution or amount of at least one analyte may thereby be detected in the sample.

The samples may be viewed using microscopy, such as fluorescent microscopy, that can excite the upconverting particles by illuminating with a particular wavelength of light. In some example a filter is used for filtering out the fluorescent light. Additionally, and/or alternatively, in some examples the filter is a time delay. The auto-fluorescent light from the background, such as from a formalin fixated and paraffin embedded tissue sample, or from the tissue sample itself, may be emitted for a shorter period of time than the fluorescent light from the particles. By not detecting or not using detected fluorescent light from a first period of time, such as 1 ms, such as 0.5 ms, such as 0.1 ms, after the excitation, the fluorescent light from the particles may be filtered out from the auto-fluorescent light of the background, i.e. the auto-fluorescent light from the background may be suppressed.

The fluorescent microscopy may be a conventional fluorescent microscopy wherein the light source and the detector has been selected to be used with the luminescent particles used. When a filter is required, the filter will also be adjusted to suit the emission spectra of the luminescent particles.

The fluorescence microscopy may be used in reflectance mode or transmission mode, or the microscopy may be a confocal fluorescent microscopy.

The fluorescent microscopy may be a microscope wherein an eye-piece is used for visually study the samples. In some examples, the microscope is in a housing generating a digitalised image that may be analysed manually or automatically using image processing algorithms.

A housing may be used to shield the sample from the ambient background light that may interfere with the detection of the fluorescent light. In some examples, a manual fluorescent microscope may also have a housing for shielding the sample when being visually analysed.

Alternatively, in some examples, techniques used for analysing the samples are described, for example, in WO2010/128090 and WO2014/006012, both which are hereby incorporated by reference in their entirety.

Figure 2:
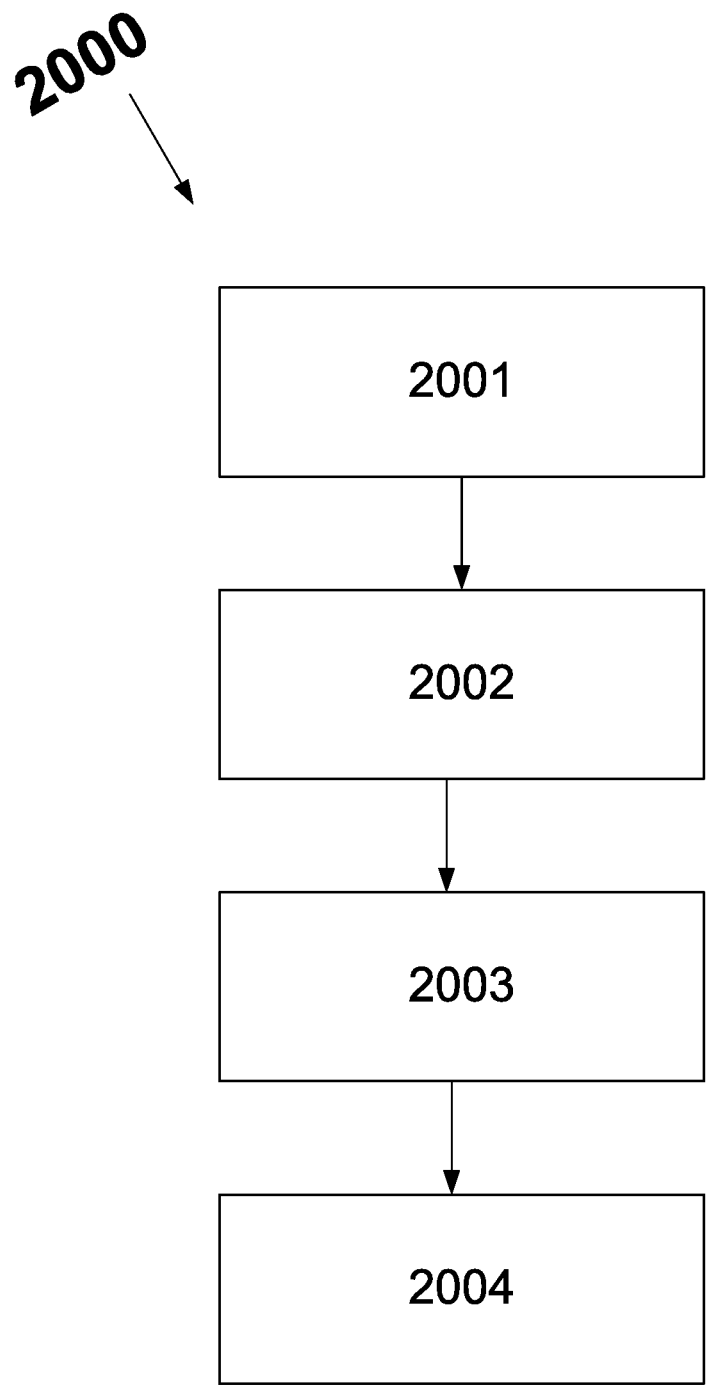
FIG. 2 is illustrating a further example of a method of analysing a sample for at least one analyte.

FIG. 2 is illustrating another method 2000 according to the disclosure. The method 2000 may include the techniques described in connection to the method of FIG. 1. FIG. 2 illustrates in particular a method 2000 of analysing a sample for at least one analyte in a biological sample. The sample may be fixated using paraffine or being frozen or free-floating. The sample could also be a liquid. The method 2000 is advantageously used for histology, such as immunohistochemistry (IHC), or cytology, such as immunocytochemistry (ICC). But may also be used for hybridizations, such as in situ hybridization (ISH) and in particular fluorescing in situ hybridization (FISH). The method includes contacting 2001 the sample with at least one targeting moiety or probe, wherein each different targeting moiety or probe of the at least one targeting moiety or probe specifically may bind a different analyte of the at least one analyte. Each different targeting moiety or probe of the at least one targeting moiety or probe may be labelled with a different luminescent particle. The luminescent particle may be an upconverting particle.

The method 2000 may further include obtaining 2002 a first image by detecting a signal from the luminescent particle associated with the at least one targeting moiety or probe bound to the sample.

The method 2000 may further include obtaining 2003 a second image from the sample, wherein the second image may be a bright-field image of the sample without counterstain, or wherein the second image is an image, of the sample being counterstained or coloured using a dye or stain.

In some examples may the second image of the counterstained sample be obtained using, for example, MUSE, bright-field or fluorescence. The detection method used depends on the type of counterstain.

The method 2000 may also include combining 2004 the first image with the second image to obtain a combined image. Additionally, in some examples the combined image is analysed for detecting the presence or amount of the at least one analyte. The detection may be qualitative or quantitative, and may also be based on the location of the detected light from the upconverting particles. The information may be combined with other detected information from the combined image, such as information from other staining methods, such as the counterstaining or traditional immunohistochemistry, immunocytochemistry, or Hybridization staining. The information may also be combined with bright-field information of the sample without counterstaining, if available.

The advantages with this method is that the same sample or section may include both the IHC staining, its counterstaining and the luminescent staining to detect the analyte. The second image which include the IHC staining and/or counterstaining may both give further information of the sample but will also give information about the morphology and/or the localisation of the targeted analytes. Since it may be done on the same sample, there is no issues with co-registration. Co-registration is an issue when different consecutive sections have to be used for the non-stained or counterstained image, and the fluorescing image used for detecting the targeted analytes. This will increase the contrast and the resolution, improving the analysis of the sample. Further, since the upconverting nanoparticles have very narrow spectral peaks, around 10 to 20 nm, the risk for overlapping is very low when using more than one label for detecting more than one analytes from the same sample or section. Hence multiplexing is possible without using multiple consecutive sections. The multiplexing on the same sample, such as section, may be done either by having all labels of the staining being upconverting particles, or a combination of upconverting particles and traditional immunohistochemistry, immunocytochemistry, or Hybridization staining, since the narrower spectral peak combined with the fluorescence at longer wavelengths reduce the risk of overlapping. This may be an advantage when a traditional immunohistochemistry, immunocytochemistry, or Hybridization staining works very well for a specific analyte but it's hard due to spectra overlapping to detect more than one analyte from the same sample using traditional staining.

The multiplexing may again improve the contrast and resolution, but most of all reduce the amount of biological sample needed. This is an advantage since most regular biopsies are small. This applies especially to immunocytochemistry or fluid cytometry where very few cells (in the range of 10) may be analysed. These cells may be extracted from a biopsy fluid. This is for example common for lung biopsy when a thin needle is employed to avoid damaging blood vessels.

The contrast and resolution may further be improved since there is no need to use common methods to reduce the auto-fluorescence which may decrease the strength of the detected fluorescence. Instead, the upconverting particles may be selected to have a fluorescence which is emitted at a longer wavelength in the near infrared or infrared region where the auto-florescence is so weak that it is neglectable or does not exist. The auto-fluorescence may be emitted for a shorter period of time than the fluorescent light from the upconverting particles, and by not detecting or not using detected fluorescent light from a first period of time, such as 1 ms, such as 0.5 ms, such as 0.1 ms, after the excitation, the fluorescent light from the particles the auto-fluorescent light may be filtered out while still detecting a strong fluorescence. Other issues related to absorbance and/or fluorescence of common stains are also reduced due to both excitation and emission with higher wavelengths.

This will make it easier to select a counterstain or a plurality of counterstains for highlighting different part of the cells structures to improve the morphology and localisation, since only the spectral overlapping of the counterstains may need to be considered. The improved contrast resolution and simple multiplexing may improve the diagnosis for immunohistochemistry, immunocytochemistry as well as for hybridizations. The increased contrast and resolution is an advantage when performing digitalization and/or automatic analysis of the images. Further, the improved contrast and resolution may also be an advantage when using artificial intelligence for the analysis combined with a reduced amount of artifacts due to no issues with co-registration.

Figure 3A:
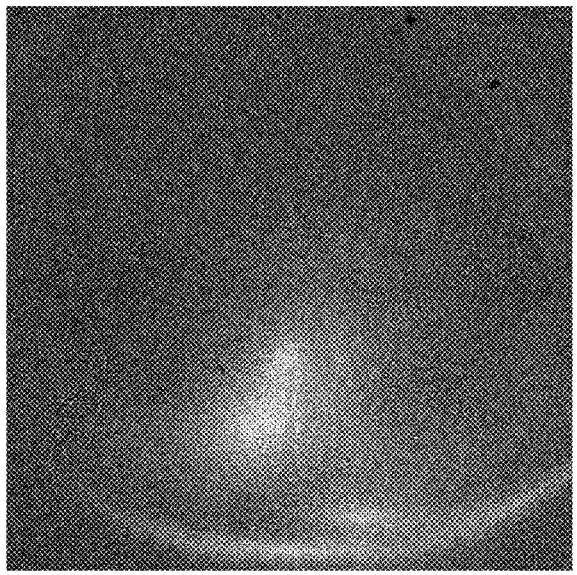
FIGS. 3A to 3C are illustrating an example of immunocytochemistry (ICC) using upconverting particles combined with a brightfield image.
Figure 3B:
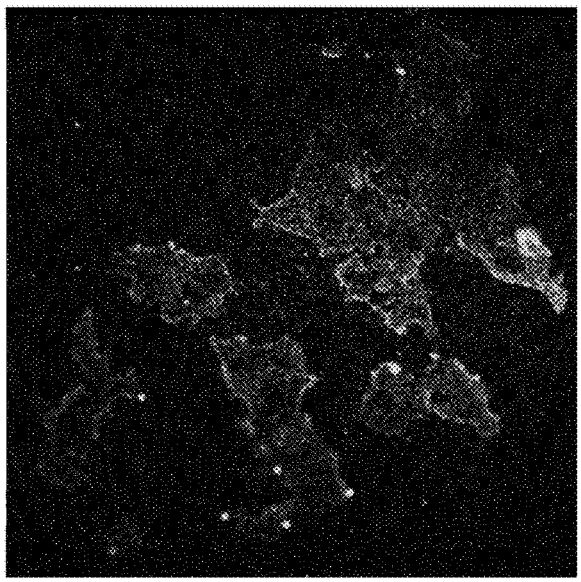
Figure 3C:
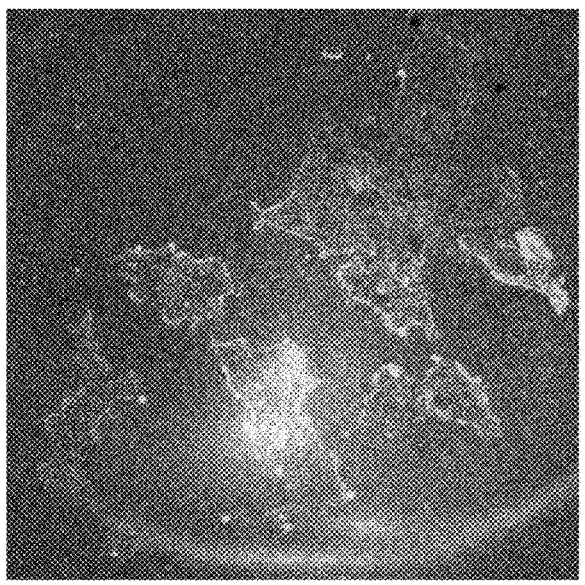

FIGS. 3A to 3C are illustrating one example of the above described method of FIG. 2 on a cultured MCF-7 cells sample using immunocytochemistry. FIG. 3A is a non-counterstained bright-field image of the sample. FIG. 3B is showing a fluorescence image of upconverting nanoparticles stained to the sample. The detection method was: mAb anti-Beta actin (Host: Mouse), and Goat anti-Mouse conjugated to the particle. The particles were Thulium doped upconverting nanoparticle or Lanthanide upconverting nanoparticle excited at 974 nm and detected below 830 nm.

FIG. 3C is showing a combined image of FIGS. 3A and 3B. It is clear form this combined that the combination gives a clear image of the localisation of the fluorescing particles in relation to the cell structures.

Figure 4A:
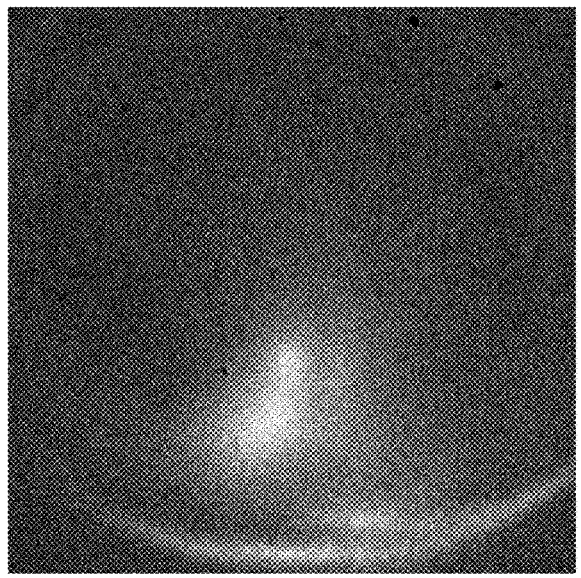
FIGS. 4A to 4C are illustrating another example of immunocytochemistry (ICC) using upconverting particles combined with a brightfield image.
Figure 4B:
Figure 4C:
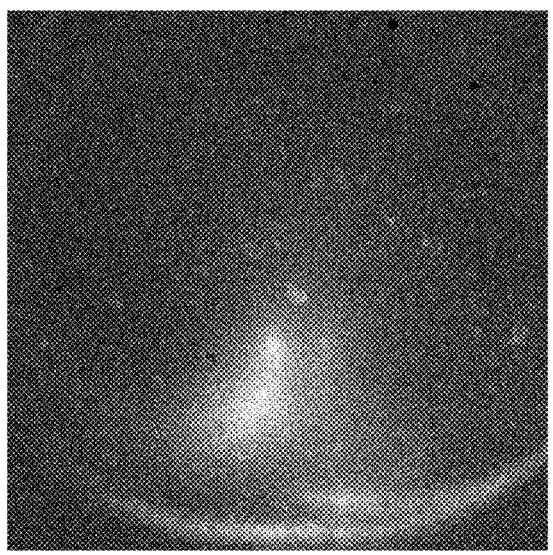

FIGS. 4A to 4C are illustrating one example of the above described method of FIG. 2 on a cultured MCF-7 cells sample using immunocytochemistry. FIG. 4A is a non-counterstained bright-field image of the sample. FIG. 4B is showing a fluorescence image of upconverting nanoparticles stained to the sample. The detection method was: mAb anti-Beta actin (host: Mouse), Biotinylated Goat anti-Mouse, and Neutravidin conjugated to the particle. The particles were Thulium doped upconverting nanoparticle or Lanthanide upconverting nanoparticle excited at 974 nm and detected below 830 nm FIG. 4C is showing a combined image of FIGS. 4A and 4B. It is clear form this combined image that the combination gives a clear image of the localisation of the fluorescing particles in relation to the cell structures.

Figure 5A:
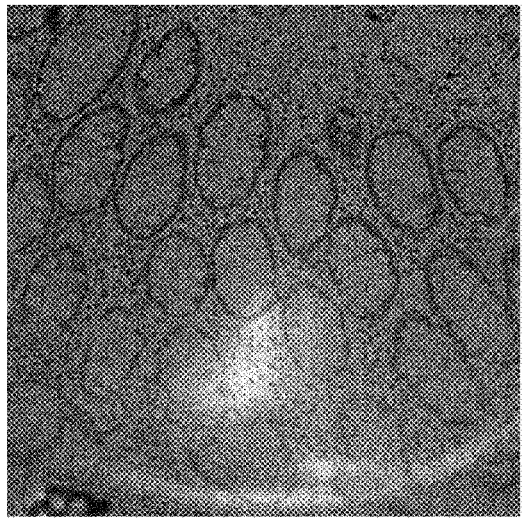
FIGS. 5A to 5C are illustrating an example of immunohistochemistry (IHC) using upconverting particles combined with a brightfield image being counterstained.
Figure 5B:
Figure 5C:
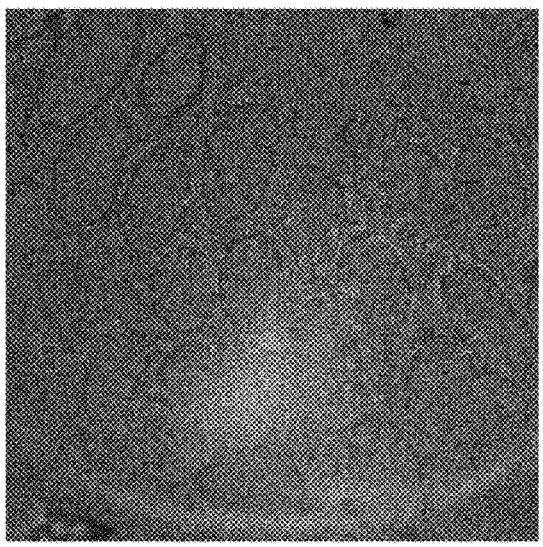

FIGS. 5A to 5C are illustrating one example of the above described method of FIG. 2 on a human colon tissue sample using immunohistochemistry as the detection method. FIG. 5A is showing a bright-field image of the sample counterstained with Haematoxylin. FIG. 5B is showing a fluorescence image of upconverting nanoparticles stained to the sample. The detection method was: mAb anti-PCK (host: Mouse), and Goat anti-Mouse conjugated to the particle). The particles were Thulium doped upconverting nanoparticle or Lanthanide upconverting nanoparticle excited at 974 nm and detected below 830 nm. FIG. 5C is showing a combined image of FIGS. 5A and 5B. It is clear from the combined image that the combination gives a high contrast image of the localisation of the fluorescing particles in relation to the cell structures.

Examples

In some examples, the targeted biomarkers may be Ku70/80, PSA, hK2 and the HER2, all expressed in prostate carcinoma to varying extents. The antibody-functionalized particles may be tumor targeting by employing tumor-specific ligands, such as antibodies, its F(ab'), F(ab')$_2$ or Fab, or small molecules which recognize tumor-associated antigens in the prostate cancer microenvironment. The advantage of this targeting compared to passive targeting (non-tumor specific biomolecule), is the highly specific interactions between the ligands and the tumor antigens, enhancing the tumor retention of the particle constructs and at the same time minimize the unspecific binding to non-target cells. Examples of ligands are:

The INCA-X antibody, a human IgG1 antibody with specificity for epitopes associated with the Ku70/Ku80 complex that has been shown to specifically bind to and rapidly internalize in an aggressive prostate cancer cell line (PC-3).

The 5A10 antibody, a murine antibody with specificity for the free prostate specific antigen, fPSA which is frequently used as in PCa diagnostics. PET-imaging using 89Zr-DFO-5A10 was successful in finding prostate cancer expressing tumors and in bone metastases in mice.

The 11B6 antibody, both in murine and humanized versions. This antibody targets the human kallikrein 2 (hK2), a protease with approximately 80% homology with PSA.

The affibody molecules are a class of small molecules that are highly specific and strong binders to the target HER2, which are overexpressed in 30% of all breast cancers and in 12-64% in prostate cancer. PET imaging of HER2 expression in breast cancer using affibody molecules are well studied and clinical studies are now ongoing.

In order to label target cells, the particles have to be functionalized with the targeting molecule on their surfaces. Antibodies, e.g. the ones mentioned above, may be used and their Fab, F(ab'), and F(ab')$_2$ fragments and Affibody molecules. In general, small molecules are attractive due to high purity and less immunogenicity. Also, the functionalized upconverting particles can be kept small (on the order of 20 nm). Successful bioconjugations of targeting moieties to the upconverting particles are important and can be done using traditional direct conjugation methods: carboxyl-modified and amine-modified chemistry (covalent) and non-covalent chemistry (relies on electrostatic binding), that are applied during particle preparation. However, direct conjugation with unmodified antibody-based targeting agents gives low incorporation efficiency. Another suitable method for attaching targeting agents to particles is the use of linker chemistry of, e.g. SMCC, NHS-PEG-MAL, SPDP linker for amine-reactive particle and NHS-ester for carboxyl-reactive particles. Recently, the evolution of bioconjugation strategies based on click chemistry have shown to give high reaction efficiency and provide more chemoselective reactions. Affibody molecules have been investigated using this method described.

While several examples of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Also, different method steps than those described above, performing the method by hardware, may be provided within the scope of the disclosure. The different features and steps of the disclosure may be combined in other combinations than those described. The scope of the disclosure is only limited by the appended patent claims.

The invention claimed is:

1. A method of imaging at least one analyte in a biological sample for histology, cytology, or hybridizations used for support in diagnosing a subject, the method comprising:
    providing said sample being a section of tissue, a sample of cells, or a liquid obtained from said subject;
    contacting said sample with at least one targeting moiety or probe, wherein each different targeting moiety or probe of said at least one targeting moiety or probe specifically binds a different analyte of the at least one analyte, and wherein each different targeting moiety or probe of said at least one targeting moiety or probe is labelled with a different luminescent particle, wherein said luminescent particle is an upconverting particle; and
    obtaining a first image by detecting a signal from said luminescent particle associated with said at least one targeting moiety or probe bound to said sample;
    obtaining a second image from said sample using brightfield and wherein said second image is an image of said sample being counterstained or colored using a dye or a stain, wherein said dye or stain is not said upconverting particle;
    combining said first image with said second image to obtain a combined bright-field and co-registered fluorescent signal image comprising both visually perceptible dye or stain under bright-field illumination and visually perceptible fluorescent signals from said upconverting particle;
    wherein the first and second images are obtained using the same section of the sample to avoid issues with co-registration of images obtained from different sections of the sample, and
    wherein the luminescent particles are co-stained with the dye or stain used for bright-field.

2. The method of claim 1, wherein each different luminescent particle emits distinguishable emission spectra.

3. The method of claim 1, wherein an excitation light for obtaining the first image is pulsed.

4. The method of claim 1, wherein said sample is formalin fixated and paraffin embedded; or wherein said sample is frozen, or wherein said sample is a free-floating section.

5. The method of claim 1, wherein said at least one targeting moiety is an analyte specific ligand.

6. The method of claim 1, wherein said at least one targeting moiety or probe is an antibody, an antigen, a hormone, a drug, a fragment antigen binding, an affibody molecule, an enzyme, a protein, a peptide, or a DNA, RNA or modified nucleic acid strand.

7. The method of claim 1, wherein said at least one targeting moiety is directly conjugated to said luminescent particle by covalent or noncovalent chemistry.

8. The method of claim 1, wherein said at least one targeting moiety is conjugated to said luminescent particle by linker chemistry.

9. The method of claim 1, comprising detecting said signal from said luminescent particle with a time delay from an excitation signal to suppress background luminescence.

10. The method of claim 1, wherein said dye or stain used for brightfield comprises Haematoxylin and/or Eosin stain, either each alone or combined.

11. The method of claim 1, wherein the method includes analyzing said combined image for detecting the presence or amount of the at least one analyte.

12. The method of claim 1, wherein said sample being counterstained or colored provides information of a morphology of the sample and/or a localization of the analyte bound to the targeting moiety or probe.

13. The method of claim 5, wherein said analyte specific ligand is a tumor specific ligand.

14. The method of claim 8, wherein said at least one targeting moiety is conjugated to said luminescent particle by an adaptor molecule to link said at least one targeting moiety to said luminescent particle.

15. The method of claim 1, wherein the dye or stain used for bright-field exhibits auto-fluorescence.

16. The method of claim 15, wherein the method is performed without performing steps to reduce an auto-fluorescent signal from the dye or stain used for bright-field.

17. The method of claim 1, wherein the method is performed without using a control probe different from the luminescent probe and the dye or stain used for bright field to provide co-registration information for the first and second images.

18. The method of claim 16, wherein the method is performed without using a control probe different from the luminescent probe and the dye or stain used for bright field to provide co-registration information for the first and second images.

19. The method of claim 1, wherein the luminescent particle emits a fluorescent signal in the near infrared or infrared region.

20. The method of claim 18, wherein the luminescent particle emits a fluorescent signal in the near infrared or infrared region.

* * * * *